United States Patent [19]
Hangay et al.

[11] Patent Number: 5,622,927
[45] Date of Patent: Apr. 22, 1997

[54] PHARMACEUTICAL COMPOSITION AND METHOD FOR TREATING VULVITIS OR VULVOVAGINITIS

[75] Inventors: György Hangay; Gáborné Olah; Edit Tókos; György Vámos, all of Budapest, Hungary

[73] Assignee: Vepex KFT., Budapest, Hungary

[21] Appl. No.: 374,572

[22] PCT Filed: Mar. 18, 1993

[86] PCT No.: PCT/HU93/00016

§ 371 Date: Aug. 16, 1995

§ 102(e) Date: Aug. 16, 1995

[87] PCT Pub. No.: WO94/02148

PCT Pub. Date: Feb. 3, 1994

[30] Foreign Application Priority Data

Jul. 22, 1992 [HU] Hungary .................. 92 02398

[51] Int. Cl.$^6$ .......................... A61K 38/00; A01N 37/18
[52] U.S. Cl. ..................... 514/2; 514/434; 514/967; 514/252; 514/625; 514/385; 514/53; 514/557; 424/697; 424/680; 424/664

[58] Field of Search .................. 514/434, 967, 514/252, 625, 385, 2, 53, 557; 424/697, 680, 664

[56] References Cited

U.S. PATENT DOCUMENTS

| | | | |
|---|---|---|---|
| 4,405,610 | 9/1983 | Krnjervic | 424/180 |
| 4,628,063 | 12/1986 | Haines et al. | 514/626 |
| 4,665,069 | 5/1987 | Rosenberg et al. | 514/222 |
| 5,466,680 | 11/1995 | Rudy | 514/57 |

*Primary Examiner*—Rebecca Cook
*Attorney, Agent, or Firm*—Birch, Stewart, Kolasch & Birch, LLP

[57] ABSTRACT

The invention relates to a pharmaceutical composition for treating the symptoms of vulvitis and vulvovaginitis which comprises folic acid, panthenol and/or allantoin, protein hydrolysate or casein hydrolysate, lactose or dextrose, lactic acid, magnesium sulfate and sodium chloride or ammonium chloride in the form of suppositories, ointments, solutions or sprays and a method of use thereof.

8 Claims, No Drawings

PHARMACEUTICAL COMPOSITION AND METHOD FOR TREATING VULVITIS OR VULVOVAGINITIS

This application is a 371 of PCT/HU93/00016 filed Mar. 18, 1993.

This invention relates to a new bioactive composition as well as the preparation and use thereof for treating the symptoms of vulvitis and vulvovaginitis (genital fluor).

The symptoms mentioned and their treatment raise a number of problems since the restoration of a health damage arising from the abnormal function of vagina is connected also with a rapid reconstitution or with the possibility of a rapid reconstitution of epitheliam tissues and not only with curing the symptoms of the disease. The character of the treatment of genital fluor is discussed by Dr. S. Gardó in two papers entitled: "The Causes and Treatment of Genital Fluor"/Magyar Noorvosok Lapja Journal of Hungarian Gynecologists) 54, pp. 7–12 (1991)/ and: "The Treatment of Genital Fluor"/ibidem 54, pp., 187–191 (1991)/.

It is known that the development or reconstitution of the appropriate normal microflora of lactobacilli in the vagina contributes to the suppression of symptoms, however, there exists several possibilities and variations for restoring the normal state and the effect of these cannot uniformly be assured in each case.

In the Hungarian patent specification No. 190,732 about hundred ingredients are described (disclosed), nearly thirty combination of which are suggested to prepare for restoration of the normal microflora in the vagina. These combinations are aimed to achieve the same effect such as the increase in the germ number of lactobacilli or the restriction of pathogenic or pseudopathogenic microorganisms, respectively however, several combinations had to be tested in a number of cases, the suppression of symptoms was lengthy from time to time or the combination did not show an adequate activity.

The assuring of absorption is also an important factor in the use of therapeutical products. According to the experience the traditional W/O and O/W type ointments and emulsions as well as aqueous or alcoholic (ethanolic) solutions do not promote and even inhibit the development of a suitable effect on treating the symptoms of vulvitis.

The present invention relates to a composition, which is in general useful for alleviating the symptoms of vulvitis and vulvovaginitis and exerts a regenerative and inuring effect, too on the epithelial tissues injured and/or irritated.

In an other aspect, the present invention relates to the stabilization and fast absorption of the composition.

For preparing the composition according to the invention comprises 0.05–0.5% by weight of folic acid, 0.25–2.5% by weight of d-panthenol, 0.15–1.5% by weight of allantoin, 0.75–7.5% by weight of protein hydrolysate or casein hydrolysate, 3.0–15.0% by weight of lactose or dextrose, 0.25–2.5% by weight of lactic acid, 0.25–2.5% by weight of magnesium sulfate and 0.75–7.5% by weight of sodium chloride or ammonium chloride mixed with a pharmaceutically acceptable carrier (vehicle) and/or auxiliaries (additives). A composition is formed being useful to treat vulvitis and vulvovaginitis or to alleviate the symptoms thereof. The composition may be in the form of a suppository ointment, solution or spray. Polyoxyethylene and polyoxyethylene sorbitan fatty acid esters are used as pharmaceutically acceptable carriers.

The suppositories contain 0.05–0.5% by weight of folic acid, 0.8–1.5% by weight of protein hydrolysate, 8–14% by weight of lactose, 1.0–2.0% by weight of lactic acid, 1.0–2.1% by weight of magnesium sulfate, 20–4.0% by weight of sodium chloride or ammonium chloride, 60.0–68.0% by weight of polyoxyethylene 1540 and 10–15% by weight of sorboxethene monolaurate. Practically, the suppositories weigh 3.5–4.0 g each.

The ointments contain 0.2% by weight of d-panthenol, 0.75–1.5% by weight of protein hydrolysate, 7–12.0% by weight of lactose, 0.5–2.0% by weight of lactic acid, 0.1–0.5% by weight of magnesium sulfate, 6.0–10.0% by weight of sorboxethene monolaurate, 25–70.0% by weight of polyoxyethylene 400 and 0.5–51.0% by weight of polyoxyethylene 1540.

The solutions or sprays, respectively contain 0.2–1.0% by weight of d-panthenol, 0.6–2.0% by weight of protein hydrolysate, 5.0–10.0% by weight of lactose, 0.5–1.0% by weight of lactic acid, 0.3–0.5% by weight of magnesium sulfate, 2.0–3.0+ by weight of sodium chloride, 44.5–50.0% by weight of polyoxyethylene 400, 7.5–12.0% by weight of sorboxethene monolaurate, optionally polyoxyethylene 4000 or 1540 as well as 19.0–33% by weight of distilled water.

The compositions are stable. As evidenced by biological experiments, they alleviate the symptoms of most various types of vaginitis and vulvitis and promote the recovery or the suppression of symptoms. An important advantage of the compositions appears therein that their use do not require any examination depending on the condition of the patient since they can commonly be used in the formulations mentioned above.

Thus, the compositions comprising the ingredients according to the invention are useful to normalize the vaginal flora, to reconstitute the microflora injured, to regenerate and inure the epithelial tissues as well as to provide a preventive (prophylactic) protection against vaginal infections.

Among the sorts of vitamin B folic acid proved to be most effective, but the determination of their suitable doses (0.001–0.1 g for each dose) or concentrations (0.03–0.3%), respectively are also important. The use of d-panthenol in a concentration of 0.5–2% (0.2–1.3 g for each dose) is also preferred.

According to our findings protein hydrolysate or casein hydrolysate are equally suitable nitrogen sources since the stability can be assured in all three cases. Lactose and in several cases dextrose are useful carbon sources.

The presence of some ions and trace elements in the "composition" is also essential. Among the cations $Na^+$, $NH_4^+$ and $Hg^{2+}$, among the anions $Cl^-$ and $SO^{2-}$ proved to be most important. Accordingly, sodium chloride and/or ammonium chloride as well as magnesium sulfate have been employed. The adjustment of pH values (to 2–3.5) and optimum concentrations (to 0.1–0.5%) of the products are of great importance. First above all, d-panthenol, allantoin and folic acid are suitable to treat the irritative symptoms occurring in consequence of the diseases and epithelial injuries of various levels: the water balance of sugars and human tissues can be reconstituted by them. Lactic acid is conveniently administered to achieve an astringent effect.

The activity of the composition is considerably depending on the formulation and selection of the preferably pharmaceutical form. Suppository, gel and solution or spray are advantageous forms. Surprisingly, the formulating materials (additives) of compositions of the invention increased the activity and insured the physical-chemical and microbiological stability of combinations of the active ingredients to a greater degree than expected.

According to our experience, the advantages of suppository masses (base) containing polyoxyethylene and polyoxyethylene fatty acid ester(s) are as follows:

a greater uptake of water and powdered materials, establishment of an optional consistency by mixing the variants of diverse molecular weights, as well as an enhanced stability of the suppository mass (base) and active ingredients incorporated therein.

Polyoxyethylene stearate (Mirj$^R$), sorbitan esters, e.g. sorbitan monolaurate (Span 20$^R$) or sorboxethene esters, such as sorboxethene monolaurate (Tween 20$^R$) as well as sorboxethene monooleate (Tween 90$^R$)may be mentioned as examples of polyoxyethylene esters.

The combinations listed hereinafter proved to be most successful:

|  | I | II |
|---|---|---|
| Sorboxethene monolaurate | 15–20% | — |
| Polyoxethylene stearate | — | 5–10% |
| Polyoxethylene glycole 1540 | 75–85% | 90–95% |

The suppository mass (base) enhanced the activity of bioactive materials since the hygroscopicity of mass (base) is a factor increasing the effect, whereby the complete dissolution of active ingredients is promoted through an increase in the volume of vaginal fluid. In addition, the suppositories exert a sustained action (a few hours in vivo) due to the slow disintegration.

An other advantage of the suppository mass (base) appears therein that it makes possible to preserve stable a microbiologically unstable system.

The gel form provides advantages being similar to those of suppositories. One type of two different gels contains about 50% of polyoxyethylene glycole 1540 and 30–35% of polyoxyethylene glycole 400, whereas the other type contains polyoxyethylene glycole 400 in its major part and only 1–2% of polyoxyethylene glycole 1540. (Macrogel)

For preparing compositions formulated in the form of solutions, optionally as mechanical sprays the ingredients, taken in amount depending on the total weight, are dissolved in the aqueous phase, polyoxyethylene glycole 400 and water, then polyoxyethylene glycole 1540 and 4000 are added.

The invention is illustrated in detail by the following Examples.

EXAMPLE 1

Suppository

| Ingredients | Composition % by weight | |
|---|---|---|
|  | 1 | 2 |
| Folic acid | 0.05 | 0.2 |
| Allantoin | — | 0.5 |
| Protein hydrolisate | 1.25 | 0.8 |
| Lactose | 14.0 | 8.0 |
| Lactic acid | 2.0 | 1.0 |
| Magnesium sulfate | 1.4 | 1.0 |
| Sodium chloride | 4.0 | 2.0 |
| Polyoxyethylene glycole 1540 | 63.0 | 66.5 |
| Polyoxyethylene-sorbitan monolaurate | 14.3 | 15.0 |
| Polyoxethylene-sorbitane monostearate | — | 5.0 |

Note:
The percentages given above refer to suppositories weighing 3.5–4.0 g each The suppositories are prepared as follows:

After mixing folic acid with an adequate amount of lactose, the remainder of lactose, magnesium sulfate and sodium chloride are successively added while stirring. Protein hydrolysate is immediately mixed to the powder mixture before preparing the suspension.

Simultaneously, after melting the polyoxyethylene glycole and polyoxyethylene glycole fatty acid esters and reaching a temperature of 60° C., lactic acid is mixed to the melt, the powder mixture is suspended in the liquid suppository base containing lactic acid, then the mass is homogenized in a colloid mill. At a temperature of about 55° C., the mass is filled into cooled moulds.

EXAMPLE 2

Ointment

| Ingredients | Composition % by weight | |
|---|---|---|
|  | 3 | 4 |
| d-Panthenol | 1.0 | 0.5 |
| Protein hydrolisate | 1.0 | 0.75 |
| Lactose | 7.0 | 12.0 |
| Lactic acid | 0.5 | 1.0 |
| Magnesium sulfate | 0.5 | 0.5 |
| Polyoxyethylene-sorbitan monolaurate | 6.0 | 10.0 |
| Polyoxyethylene glycole 400 | 31.0 | 25.75 |
| Polyoxyethylene glycole 1540 | 51.0 | 42.0 |
| Condensate of hydrogenated castor oil with ethylene oxide (40 moles) | — | 3.5 |

After cooling to about 50° C. the melt of polyoxyethylene glycole and polyoxyethylene-glycole fatty acid esters, optionally a condensate of hydrogenated castor oil with ethylene oxide, panthenol is firstly dissolved in the melt and after cooling the mass further to 40°–45° C., the powder materials appropriately milled (to a sieve size of VI) and previously mixed together are suspended therein. Finally, lactic acid is mixed thereto and the system is stirred until the complete cooling down.

EXAMPLE 3

Solution or spray.

| Ingredients | Composition % by weight | |
|---|---|---|
|  | 5 | 6 |
| d-Panthenol | 0.2 | 1.0 |
| Protein hydrolisate | 0.6 | 2.0 |
| Lactose | 5.0 | 10.0 |
| Lactic acid | 0.5 | 0.5 |
| Magnesium sulfate | 0.5 | 0.3 |
| Sodium chloride | 2.0 | 3.0 |
| Allantoin | — | 0.2 |
| Polyoxyethylene-glycole 400 | 46.5 | 49.5 |
| Polyoxyethylene-sorbitan monolaurate | 12.0 | 7.5 |
| Polyoxyethylene-sorbitan monooleate | — | 2.0 |
| Distilled water | 32.7 | 24.0 |

The powdered ingredients and panthenol are successively portionwise added to the distilled water warmed to a temperature of about 60° C. Simultaneously, the ingredients of the "fatty phase" are melted. The two phases are mixed at a temperature of about 60° C. and stirred then until it cools down.

EXAMPLE 4

The clinical investigation of suppositories according to Example 1 was simultaneously carried out in the Department of Obstetrics and Gynecology of the Semmelweirs Medical University (SOTE) Budapest, Hungary as well as in the Department of Obstetrics and Gynecology of the Szent-Györgyi Albert Medical University (SZOTE) Szeged, Hungary. The clinical examinations were aimed to determine the effectivity of the suppositories and to prove that the efficiency of the treatment reached or exceeded the efficiency level of the standard treatment used in the gynecology.

The complex trial was extended to the so-called purity examination of the vagina, cultivation of bacteria and fungi, as well as to the colposcopic and cytologic tests, bimanual gynecologic examination, determination of the pH values and evaluation of subjectively judged complaints. A significant change under effect of the treatment was stated in the values of the persons examined. The changes in the cervix, vagina and vulva were evaluated on basis of the trial of SOTE before and after the treatment. The results are summarized in Table I.

TABLE I

Change in the pH values on effect of treatment

| Treatment | Before treatment | | | After treatment | | |
|---|---|---|---|---|---|---|
| | Cervix | Vagina | Vulva | Cervix | Vagina | Vulva |
| Suppository of invention | 5.00 ± 0.50 | 4.77 ± 0.64 | 4.85 ± 0.69 | 4.59 ± 0.47 | 4.42 ± 0.60 | 4.27 ± 0.60 |
| Standard treatment | 4.82 ± 0.59 | 4.69 ± 0.60 | 4.70 ± 0.54 | 4.52 ± 0.58 | 4.39 ± 0.58 | 4.35 ± 0.67 |

It is obvious from the results that the pH values were shifted to negative direction by the suppository of the invention at all the three sites of the examinations.

It has to be considered on the evaluation that the carrying-out of the (standard) treatment known in the art requires complicated, circuitous and professional instructions for the patient.

The examinations of SZOTE were aimed to control the vagina. These results are summarized in Table II. The results of check examinations performed by one month following the treatment are also shown in column 3 of Table II.

TABLE II

Changes in the pH values immediately and by one month, respectively after treatment

| Treatment | Before treatment | Immediately after treatment | By 1 month after treatment |
|---|---|---|---|
| Suppository of the invention | 5.87 ± 0.98 | 5.28 ± 0.65 | 5.43 ± 0.25 |
| Standard treatment | 6.48 ± 1.33 | 5.47 ± 0.66 | 6.07 ± 0.61 |

The effectivity of the suppository is proved also by the results of Table II. The duration of effect shows significant differences from the (standard) method of treatment known in the art.

The development of subjective complaints is illustrated in Table III on basis of the examinations of SOTE. The four syndromes, i.e. irritation, pain, rubor and discharge were evaluated both by the patients and physicians concerned.

The severity of syndromes was expressed by the following score:
0=free from complaints; 1=mild complaints;
2=moderate complaints; 3=severe complaints.

TABLE III

Evaluation by scoring the subjective parameters

| | Suppository | | | | (Traditional) treatment known in the art | | | |
|---|---|---|---|---|---|---|---|---|
| | Before treatment | | after treatment | | before treatment | | after treatment | |
| Syndrome | patient | physician | patient | physician | patient | physician | patient | physician |
| Irritation | | | | | | | | |
| 0 | 8 | 20 | 24 | 26 | 7 | 20 | 15 | 22 |
| 1 | 17 | 7 | 3 | 1 | 12 | 4 | 12 | 5 |
| 2 | 2 | — | — | — | 8 | 3 | — | — |
| 3 | — | — | — | — | — | — | — | — |
| Pain | | | | | | | | |
| 0 | 19 | — | 26 | — | 15 | — | 25 | — |
| 1 | 6 | — | 1 | — | 12 | — | 2 | — |
| 2 | — | — | — | — | — | — | — | — |
| 3 | — | — | — | — | — | — | — | — |
| Discharge | | | | | | | | |
| 0 | 4 | 1 | 5 | 6 | 2 | 3 | 6 | 4 |
| 1 | — | 1 | 19 | 15 | 1 | 1 | 16 | 14 |

TABLE III-continued

| | Evaluation by scoring the subjective parameters | | | | | | | |
|---|---|---|---|---|---|---|---|---|
| | Suppository | | | | (Traditional) treatment known in the art | | | |
| | Before treatment | | after treatment | | before treatment | | after treatment | |
| Syndrome | patient | physician | patient | physician | patient | physician | patient | physician |
| 2 | 20 | 20 | 2 | 4 | 15 | 19 | 5 | 9 |
| 3 | 3 | 3 | 1 | — | 9 | 5 | — | — |
| Rubor | | | | | | | | |
| 0 | 1 | 3 | 14 | 13 | 2 | 4 | 13 | 11 |
| 1 | 16 | 12 | 13 | 12 | 13 | 10 | 13 | 13 |
| 2 | 10 | 12 | — | 2 | 11 | 13 | 1 | 3 |
| 3 | — | — | — | — | 1 | — | — | — |

It can be pointed out in relation to the subjective complaints that the improvement in all the four syndromes, especially in the cases of irritation, pain and discharge was significant. A significant alleviation of complaints was observed by the joint evaluation of complaints.

We claim:

1. A pharmaceutical composition for treating the symptoms of vulvitis or vulvovaginitis, which comprises as active ingredients 0.05–0.5% by weight of folic acid, 0.25–2.5% by weight of d-panthenol or 0.15–1.5% by weight of allantoin or a mixture of panthenol and allantoin, 0.75–7.5% by weight of protein hydrolysate or casein hydrolysate, 3.0–15.0% by weight of lactose or dextrose, 0.25%–2.5% by weight of lactic acid, 0.25–2.5% by weight of magnesium sulfate and 0.75–7.5% by weight of sodium chloride or ammonium chloride in an admixture with a pharmaceutically acceptable carrier.

2. A composition as claimed in claim 1, in which the pharmaceutically acceptable carrier is selected from the group consisting of polyoxyethylene glycol and a polyoxyethylene sorbitan fatty acid ester or a mixture thereof.

3. A composition for treating the symptoms of vulvitis or vulvovaginitis in the form of a suppository, which comprises 0.05–0.1% by weight of folic acid, 0.8–1.5% by weight of protein hydrolysate, 8–14% by weight of lactose, 1.0–2.0% by weight of lactic acid, 1.0–2.1% by weight of magnesium sulfate, 2.0–4.0% by weight of sodium chloride or ammonium chloride, 60.0–68.0% by weight of polyoxyethyleneglycol 1540 and 10–15% by weight of polyoxyethyleneglycol monolaurate.

4. An ointment composition for treating the symptoms of vulvitis or vulvovaginitis which comprises 0.2% by weight of d-panthenol, 0.75–1.5% by weight of protein hydrolysate, 7–12.0% by weight of lactose, 0.5–2.0% by weight of lactic acid, 0.1–0.5% by weight of magnesium sulfate, 6.0–10.0% by weight of polyoxyethylene glycol monolaurate, 25–70.0% by weight of polyoxyethylene glycol 400 and 0.5–51.0% by weight of polyoxyethylene glycol 1540.

5. A solution or spray composition for treating the symptoms of vulvitis or vulvovaginitis which comprises 0.2–1.0% by weight of d-panthenol, 0.6–2.0% by weight of protein hydrolysate, 5.0–10.0% by weight of lactose, 0.5–1.0% by weight of lactic acid, 0.3–0.5% by weight of magnesium sulfate, 2.0–3.0% by weight of sodium chloride, 44.5–50.0% by weight of polyoxyethylene glycole 400, 7.5–12.0% by weight of polyoxyethylene-glycole monolaurate, and 19.0–33% by weight of distilled water.

6. A process for the preparation of the pharmaceutical composition of claim 1, which comprises mixing 0.05–0.5% by weight of folic acid, 0.25–2.5% by weight of d-panthenol or 0.15–1.5% by weight of allantoin or a mixture of panthenol and allantoin, 0.75–7.5% by weight of protein hydrolysate or casein hydrolysate, 3.0–15.0% by weight of lactose or dextrose, 0.25%–2.5% by weight of lactic acid, 0.25–2.5% by weight of magnesium sulfate and 0.75–7.5% by weight of sodium chloride or ammonium chloride with a pharmaceutically acceptable carrier.

7. The process as claimed in claim 6, in which the pharmaceutically acceptable carrier is selected from the group consisting of polyoxyethylene glycol and a polyoxyethylene glycol sorbitan fatty acid ester or a mixture thereof.

8. A method for the treatment of symptoms of vulvovaginitis and vulvitis which comprises administering to a patient an effective amount of the composition of claim 1.

* * * * *